United States Patent [19]

Decor

[11] 4,111,998
[45] Sep. 5, 1978

[54] PROCESS FOR THE PREPARATION OF AROMATIC ALDEHYDES

[75] Inventor: Jean-Pierre Decor, Villeurbanne, France

[73] Assignee: Rhone-Poulenc S.A., Paris, France

[21] Appl. No.: 489,715

[22] Filed: Jul. 18, 1974

[30] Foreign Application Priority Data

Jul. 20, 1973 [FR] France .................. 73 26713

[51] Int. Cl.² .............................................. C07C 47/48
[52] U.S. Cl. ................................ 260/599; 260/600 R
[58] Field of Search ............................... 260/599, 600

[56] References Cited

U.S. PATENT DOCUMENTS 3,517,066  6/1970  Gurien et al. .................. 260/599

OTHER PUBLICATIONS

White et al., J. of Lipid Resh. vol. 8, pp. 158–160 (1967).
Wagner et al., Synthetic Organic Chem., Wiley & Sons, pp. 291–292 (1965).
Ferguson, The Synthesis of Aromatic Aldehydes, Chem. Reviews, vol. 38, p. 243 (1946).

*Primary Examiner*—James O. Thomas, Jr.
*Assistant Examiner*—G. T. Breitenstein
*Attorney, Agent, or Firm*—Cushman, Darby & Cushman

[57] ABSTRACT

A process is provided for the preparation of a juxtanuclear or extranuclear aromatic aldehyde, said process comprising effecting the catalytic reduction of the corresponding acid chloride using hydrogen in the presence of a palladium catalyst and a tertiary amide. The use of the tertiary amide increases the selectivity, activity and working life of the catalyst as compared with conventional processes and renders the use of catalyst regulators such as quinoline or sulphur-containing compounds unnecessary.

11 Claims, No Drawings

PROCESS FOR THE PREPARATION OF AROMATIC ALDEHYDES

The present invention relates to an improvement in the process for the preparation of aldehydes by reduction of organic acid chlorides by means of hydrogen and in the presence of a palladium catalyst.

The reduction of acid chlorides to the corresponding aldehydes by means of hydrogen in the presence of palladium is a process which is well known to those skilled in the art and which involves the reaction commonly known as the ROSENMUND reaction. The essential characteristic of this process is the use of a palladium-based catalyst, the activity of which is generally reduced by poisoning with quinoline or sulphur-containing compounds. The presence of these inhibitors or regulators makes it possible to render the reaction selective, by limiting to a very large extent the subsequent reduction of the aldehyde to the corresponding alcohol and hydrocarbon; thus the selectivity of the catalyst is increased but at the same time its activity and its resistance to aging is decreased. In order to increase the yield of aldehyde, it has also been proposed to employ, at the same time as the usual catalyst regulators (quinoline or sulphur-containing compounds), alkali metal salts of organic acids which "fix" the hydrochloric acid liberated (see U.S. Pat. No. 3,517,066).

The present invention provides a process for the preparation of an aromatic aldehyde by reduction of the corresponding acid chloride by means of hydrogen and in the presence of a palladium catalyst, the reaction being carried out in the presence of a tertiary amide. The process is suitable for the preparation of juxtanuclear aromatic aldehydes (i.e. aldehydes in which the carbon atom of the aldehyde group is adjacent to a ring member of the aromatic nucleus) and extranuclear aromatic aldehydes (i.e. aldehydes in which the carbon atom of the aldehyde group is separated from the aromatic nucleus by one or more atoms which do not form part of the aromatic nucleus). Furthermore, the process is suitable for the preparation of aromatic aldehydes which contain more than one aldehyde group as well as those which contain only one aldehyde group.

The process of the invention makes it possible to carry out the reduction at a moderate temperature with increased selectivity, using only a small amount of catalyst. Furthermore, the fact that quinoline or sulphur-containing compounds need not be introduced means that the catalyst is more active and has a longer working life than in the conventional process.

Suitable tertiary amides for use in the process of the invention are linear or branched amides or cycloaliphatic amides. The preferred amides are those of the formula:

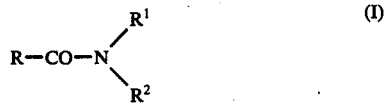

in which $R^1$ and $R^2$ each independently represents a straight or branched saturated aliphatic group with at most 6 carbon atoms, a cycloaliphatic group with 5 or 6 carbon atoms in the ring, a phenyl group or a phenylalkyl or alkylphenyl group in which the alkyl portion contains at most 4 carbon atoms, or $R^1$ and $R^2$ together form a saturated or unsaturated divalent radical such that the ring which they form together with the nitrogen atom to which they are attached contains 4 or 5 carbon atoms, and R is as defined for $R^1$ and $R^2$ when taken separately, or represents a hydrogen atom, or R, together with one of the radicals $R^1$ or $R^2$, forms a divalent radical such that the ring which they form together with the —CO—N— grouping contains 4 to 6 carbon atoms.

The most preferred amides of general formula (I) are those in which $R^1$ and $R^2$ each independently represents a straight or branched alkyl group with at most 4 carbon atoms and R represents a hydrogen atom as is defined for $R^1$ and $R^2$, or cyclic amides in which one of the radicals $R^1$ and $R^2$ represents a straight or branched alkyl group with at most 4 carbon atoms and the other of these radicals, together with the radical R, forms a divalent radical with 3 to 5 carbon atoms.

Specific examples of such amides are N,N-dimethylformamide, N,N-dimethylpropionamide, N,N-dimethylisobutyramide, N,N-dimethylacetamide, N,N-diethylacetamide, N,N-dibutylacetamide, N-methylpyrrolidone, N-ethylpyrrolidone, N-methylpiperidone, N-methylcaprolactam, N-methylformanilide, N-methylacetanilide, N-acetylpyrrolidine and N-acetylpyridine.

N,N-dimethylformamide, N,N-dimethylacetamide and N-methylpyrrolidone, which are commonly used in industry, are particularly suitable.

The amount of tertiary amide which is used varies depending on the nature of the acid chloride employed. When aromatic acid chlorides which contain only one chloroformyl group are reduced, great improvements in selectivity can be obtained even when only small amounts of tertiary amide, for example from $10^{-5}$ to $10^{-1}$ mol of tertiary amide per mol of acid chloride to be reduced, are used. When the aromatic acid chlorides contain several chloroformyl groups in the same molecule, it may be necessary to use larger amounts of tertiary amide. These amounts can be determined easily by those skilled in the art, if necessary by means of preliminary experiments. The tertiary amide can act as the solvent in the reaction, but when only a small amount of tertiary amide is used, it is also possible to carry out the reduction reaction in the presence of an independent solvent. Examples of suitable solvents are hydrocarbons such as xylene, toluene, benzene, tetralin and decalin, or ethers such as dioxane.

The preferred aromatic acid chlorides containing only one chloroformyl group are those of the following formula:

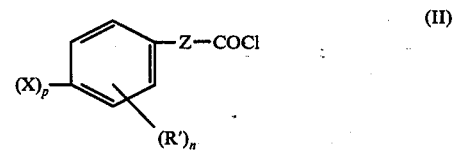

in which n and p each independently is 0, 1 or 2, R' is a straight or branched alkyl group with at most 4 carbon atoms, or if n is 2 and the two radicals R' are adjacent, they can, taken together, form an unsaturated divalent group which has 4 carbon atoms and which, together with the two carbon atoms of the benzene ring, forms another benzene ring, X is a hydroxyl, alkoxy, cycloalkoxy or phenoxy group, and Z is a valency bond or a saturated or unsaturated divalent hydrocarbon radical with at most 6 carbon atoms.

Preferably, p and n each independently is 0 or 1, Z represents a valency bond, X represents a hydroxyl group or an alkoxy group with at most 6 carbon atoms, and R' represents a straight or branched alkyl group with at most 4 carbon atoms.

Specific examples of acid chlorides of formula (II) are the chlorides of the following carboxylic acids: benzoic acid, methylbenzoic acid, dimethylbenzoic acid, methyl-isopropylbenzoic acid, salicylic acid, p-hydroxybenzoic acid, anisic acid, acetylsalicylic acid, phenoxybenzoic acid, 5-ethyl-2-hydroxy-benzoic acid, 5,6-dimethyl-2-hydroxy-benzoic acid, 5-butyl-2-hydroxy-benzoic acid, 3-methoxy-salicylic acid, cresotinic acids, 2,4-dihydroxy-benzoic acid, vanillic acid, isovanillic acid, phenylacetic acid, phenylpropionic acid, phenylbutyric acid, phenylacrylic acid, cinnamic acid and phenylpropiolic acid.

As has already been stated, the process of the invention can also be used for the reduction of acid chlorides containing several chloroformyl groups in the molecule; typical such chlorides are those of terephthalic acid, 4,4'-dicarboxy-diphenylmethane and 4,4'-dicarboxydiphenyl ether.

The amount of palladium-based catalyst employed is not critical, but it is usually from 0.05 to 1 g., preferably from 0.1 to 0.5 g., of palladium per mole of acid chloride.

The catalyst is preferably deposited on a support, the proportion of palladium suitably being from 0.5 and 25% by weight on the weight of the support. The nature of the support is not critical; examples of supports which may be used are active charcoal, alumina or silica. It is also possible to use catalysts based on palladium deposited on barium sulphate or calcium sulphate.

The process of the invention is suitably carried out in a stream of hydrogen, the apparatus being at atmospheric pressure. The reaction can also be carried out in a closed vessel, under a hydrogen pressure greater than atmospheric pressure. The temperature is preferably from 20° to 150° C., especially from 50° to 80° C.

The following Examples illustrate the invention. Percentages are by weight.

EXAMPLE 1

900 ml. of toluene, 5 g. of catalyst consisting of palladium deposited on carbon black (10% of metal) and 15 microlitres of N,N-dimethylformamide are placed in a flask and a uniform stream of hydrogen is passed through the mixture. The contents of the flask are then heated to 44° C., and, whilst keeping them at this temperature, a mixture of 156.5 g. of salicyloyl chloride and 100 ml. of toluene is run in over the course of 10 minutes. The flask is then kept at 44° C. for 3½ hours until hydrogen chloride ceases to be evolved.

After filtering off the catalyst and washing it with 200 ml. of toluene, the salicylaldehyde is measured by converting it to the oxime and by vapour phase chromatography. By means of the two methods, it is established that the degree of conversion is 98% and that the yield of aldehyde of 87.5%.

On distillation, 99 g. of a fraction which boils at 59°–60° C. under 3.5 mm.Hg and which contains 99.3% of salicylaldehyde, are obtained.

EXAMPLE 2

Following the procedure of Example 1, 0.05 mol of salicyloyl chloride is hydrogenated, all the other parameters of the reaction (ratios of the reagents, temperature etc.) remaining unchanged. The amount of N,N-dimethylformamide is varied in a series of experiments; the results are given in the following Table:

| Experiment No. | Amount of Dimethyl-Formamide (*) | DC (**) | Yield of salicylaldehyde | Duration |
| --- | --- | --- | --- | --- |
| 1 (control) | 0 | 97% | 65% | 2 hrs. |
| 2 | $0.7 \times 10^{-3}$ | 94.7% | 82% | 2 hrs. |
| 3 | $1.4 \times 10^{-3}$ | 95.1% | 82.5% | 2 hrs. |

*The amount of dimethylformamide is expressed in mols per mol of acid chloride employed.
**DC = degree of conversion of the acid chloride.

EXAMPLE 3

700 ml. of toluene, 1.25 g. of catalyst consisting of palladium deposited on carbon black (10% of metal) and 34.7 microlitres of N,N-dimethylacetamide are placed in a flask and a uniform stream of hydrogen is passed through it. The contents of the flask are then heated to 70° C. and, whilst keeping them at this temperature, a mixture of 170.6 g. of anisoyl chloride and 300 ml. of toluene is run in over the course of 10 minutes. Hydrogen chloride ceases to be evolved after a period of 2½ hours. After filtering off the catalyst, it is found that the degree of conversion of anisoyl chloride is 90% and that the yield of anisaldehyde is 81%.

The filtrate is washed with an aqueous solution of sodium carbonate (10% solution). On distillation under reduced pressure, 101.7 g. of a fraction which boils at 69°–69.6° C. under 0.5 mm.Hg are obtained. The aldehyde content is 100%.

EXAMPLE 4

A series of experiments in which anisoyl chloride is reduced is carried out, varying the nature and the amount of tertiary amide. The results are given in the following Table:

| Experiment No. | Nature of the amide | Mols of amide g of catalyst | DC | Yield of anisaldehyde |
| --- | --- | --- | --- | --- |
| 1 | Dimethylformamide | $0.77 \times 10^{-4}$ | 98% | 73.5% |
| 2 | " | $1.6 \times 10^{-4}$ | 98% | 77% |
| 3 | N-methylpyrrolidone | $0.78 \times 10^{-4}$ | 99% | 74% |
| 4 | " | $1.25 \times 10^{-4}$ | 98% | 74.6% |
| 5 | " | $1.55 \times 10^{-4}$ | 92% | 77% |
| 6 | Dimethylacetamide | $0.77 \times 10^{-4}$ | 99% | 77.6% |
| 7 | " | $1.6 \times 10^{-4}$ | 99% | 86 |
| 8 | " | $3 \times 10^{-4}$ | 100% | 89.1% |
| 9 (Control) | No amide | 0 | 94% | 63% |

EXAMPLE 5

A series of experiments involving the hydrogenation of anisoyl chloride is carried as described in Example 3, using the same catalyst. When the catalyst is recycled three times, the following results are obtained:

| Experiment No. | Catalyst | DC | Yield of anisaldehyde | Duration |
|---|---|---|---|---|
| 1 | new | 99% | 82% | 3 hrs. |
| 2 | 1st recycling | 98% | 84% | " |
| 3 | 2nd recycling | 98.4% | 85.4% | " |
| 4 | 3rd recycling | 98% | 86% | " |

I claim:

1. In a process for the preparation of a juxtanuclear or extranuclear aromatic aldehyde in the liquid phase which comprises effecting the catalytic reduction with hydrogen in the presence of a palladium catalyst of an acid chloride of formula:

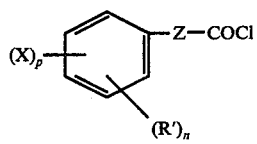

in which $n$ and $p$ each independently is 0, 1 or 2, R' is a straight or branched alkyl group with at most 4 carbon atoms, or if $n$ is 2 and the two radicals R' are adjacent, they can, taken together, form an unsaturated divalent group which has 4 carbon atoms and which, together with the two carbon atoms of the benzene ring, forms another benzene ring, X is an alkoxy or cycloalkoxy group with up to 6 carbon atoms or a phenoxy group and Z is a valency bond or a saturated or unsaturated divalent hydrocarbon radical with at most 6 carbon atoms, the improvement wherein the reduction is carried out in the presence of a tertiary amide of the formula

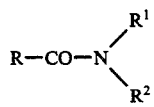

in which $R^1$ and $R^2$ each independently represents a straight or branched saturated aliphatic group with at most 6 carbon atoms, a cycloaliphatic group with 5 or 6 carbon atoms in the ring, a phenyl group or a phenylalkyl or alkylphenyl group in which the alkyl portion contains at most 4 carbon atoms, or $R^1$ and $R^2$ together form a saturated or unsaturated divalent radical such that the ring which they form together with the nitrogen atom to which they are attached contains 4 or 5 carbon atoms, and R represents a hydrogen atom, a straight or branched saturated aliphatic group with at most 6 carbon atoms, a cycloaliphatic group with 5 or 6 carbon atoms in the ring, a phenyl group or a phenylalkyl or alkylphenyl group in which the alkyl portion contains at most 4 carbon atoms, or R, together with one of the radicals $R^1$ or $R^2$ forms a divalent radical such that the ring which they form together with the —CO—N grouping contains 4 to 5 carbon atoms, the tertiary amide being present in an amount from $10^{-5}$ to $10^{-1}$ moles per mole of acid chloride.

2. A process according to claim 1 in which $R^1$ and $R^2$ each independently represents a straight or branched alkyl group with at most 4 carbon atoms and R represents a hydrogen atom or a straight or branched alkyl group with at most 4 carbon atoms, or one of the radicals $R^1$ and $R^2$ represents a straight or branched alkyl group with at most 4 carbon atoms and the other of these radicals, together with the radical R, forms a divalent radical with 3 to 5 carbon atoms.

3. A process according to claim 2 wherein the tertiary amide is N,N-dimethylformamide, N,N-dimethylacetamide or N-methylpyrrolidone.

4. A process according to claim 1 in which p and n each independently is 0 or 1, Z is a valency bond, X is an alkoxy group with at most 6 carbon atoms and R' is a straight or branched alkyl group with at most 4 carbon atoms.

5. A process according to claim 1 wherein the amount of palladium used is 0.05 to 1 g. of palladium per mole of acid chloride.

6. A process according to claim 1, wherein the amount of palladium is from 0.05 – 1 g per mole of acid chloride and the reduction is carried out in the temperature from 20° – 150° C.

7. A process according to claim 6 for the preparation of an aromatic aldehyde which comprises effecting the catalytic reduction of an acid chloride of formula:

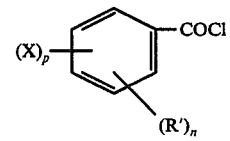

in which $p$ and $n$ each independently is 0 or 1, X is an alkoxy group with at most 6 carbon atoms and R' is a straight or branched alkyl group with at most 4 carbon atoms, using hydrogen in the presence of 0.1 to 0.5 g. of palladium per mole of acid chloride and $10^{-5}$ to $10^{-1}$ mol per mol of acid chloride of N,N-dimethylformamide, N,N-dimethylacetamide or N-methylpyrrolidone, the reaction being carried out at a temperature from 20° to 150° C.

8. In a process for the preparation of a juxtanuclear or extranuclear aromatic aldehyde in the liquid phase which comprises effecting the catalytic reduction with hydrogen in the presence of a palladium catalyst of an acid chloride of formula:

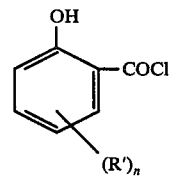

in which $n$ is 0, 1 or 2, R' is a straight or branched alkyl group with at most 4 carbon atoms, or if n is 2 and the two radicals R' are adjacent, they can, taken together, form an unsaturated divalent group which has 4 carbon atoms and which, together with the two carbon atoms of the benzene ring, forms another benzene ring, the improvement wherein the reduction is carried out in the presence of a tertiary amide of the formula

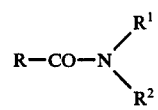

in which $R^1$ and $R^2$ each independently represents a straight or branched saturated aliphatic group with at most 6 carbon atoms, a cycloaliphatic group with 5 or 6 carbon atoms in the ring, a phenyl group or a phenylalkyl or alkylphenyl group in which the alkyl portion contains at most 4 carbon atoms, or $R^1$ and $R^2$ together form a saturated or unsaturated divalent radical such that the ring which they form together with the nitrogen atom to which they are attached contains 4 or 5 carbon atoms, and R represents a hydrogen atom, a straight or branched saturated aliphatic group with at most 6 carbon atoms, a cycloaliphatic group with 5 or 6 carbon atoms in the ring, a phenyl group or a phenylalkyl or alkylphenyl group in which the alkyl portion contains at most 4 carbon atoms, or R, together with one of the radicals $R^1$ or $R^2$ forms a divalent radical such that the ring which they form together with the —CO—N grouping contains 4 to 6 carbon atoms, the amount of tertiary amide used being from $10^{-5}$ to $10^{-1}$ moles per mole of acid chloride.

9. A process according to claim 8, wherein the tertiary amide is N,N-dimethylformamide, N,N-dimethylacetamide or N-methylpyrrolidone.

10. A process according to claim 8, wherein the amount of palladium used is 0.05 to 1 g of palladium per mole of acid chloride.

11. A process according to claim 8, wherein the amount of palladium is from 0.05 – 1 g per mole of acid chloride and the reduction is carried out in the temperature from 20° – 150° C.

* * * * *